(12) United States Patent
Floume et al.

(10) Patent No.: US 8,777,945 B2
(45) Date of Patent: Jul. 15, 2014

(54) METHOD AND SYSTEM FOR MONITORING TISSUE DURING AN ELECTROSURGICAL PROCEDURE

(75) Inventors: Timmy Floume, London (GB); Richard R. A. Syms, London (GB); George Hanna, Scotland (GB)

(73) Assignee: Covidien LP, Mansfield, MA (US)

( * ) Notice: Subject to any disclaimer, the term of this patent is extended or adjusted under 35 U.S.C. 154(b) by 986 days.

(21) Appl. No.: 12/665,081

(22) PCT Filed: Jan. 30, 2008

(86) PCT No.: PCT/US2008/052460
§ 371 (c)(1),
(2), (4) Date: May 4, 2010

(87) PCT Pub. No.: WO2009/005850
PCT Pub. Date: Jan. 8, 2009

(65) Prior Publication Data
US 2010/0217258 A1    Aug. 26, 2010

Related U.S. Application Data

(60) Provisional application No. 60/937,707, filed on Jun. 29, 2007.

(51) Int. Cl.
*A61B 18/14* (2006.01)
(52) U.S. Cl.
USPC ................................. 606/51; 606/52; 606/34
(58) Field of Classification Search
USPC ......................................... 606/32–35, 50–52
See application file for complete search history.

(56) References Cited

U.S. PATENT DOCUMENTS

| | | | |
|---|---|---|---|
| 4,016,881 | A | 4/1977 | Rioux et al. |
| D263,020 | S | 2/1982 | Rau, III |
| D295,893 | S | 5/1988 | Sharkany et al. |
| D295,894 | S | 5/1988 | Sharkany et al. |
| 5,176,695 | A | 1/1993 | Dulebohn |
| 5,318,589 | A | 6/1994 | Lichtman |
| D348,930 | S | 7/1994 | Olson |
| 5,334,183 | A | 8/1994 | Wuchinich |
| 5,336,221 | A | 8/1994 | Anderson |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

Wald et al., "Accidental Burns", JAMA, Aug. 16, 1971, vol. 217, No. 7, pp. 916-921.

(Continued)

*Primary Examiner* — Michael Peffley

(57) ABSTRACT

A system for monitoring and/or controlling tissue modification during an electrosurgical procedure includes an electrosurgical apparatus connected to an electrosurgical generator and configured to grasp tissue therebetween via a pair of jaw members. The system also includes an optical system having an optical source that directs light through tissue. One or more optical detectors analyze the light transmitted through and reflected back from the tissue and a processor utilizes this information to control the delivery of electrosurgical energy from the electrosurgical generator to the tissue.

21 Claims, 5 Drawing Sheets

(56) References Cited

U.S. PATENT DOCUMENTS

| | | | |
|---|---|---|---|
| 5,395,360 A | 3/1995 | Manoukian | |
| 5,405,344 A | 4/1995 | Williamson et al. | |
| 5,454,809 A | 10/1995 | Jansson | |
| 5,626,578 A | 5/1997 | Tihon | |
| D384,413 S | 9/1997 | Zlock et al. | |
| 5,762,609 A * | 6/1998 | Benaron et al. | 600/473 |
| 5,827,323 A | 10/1998 | Klieman et al. | |
| 5,921,916 A | 7/1999 | Aeikens et al. | |
| D424,694 S | 5/2000 | Tetzlaff et al. | |
| D425,201 S | 5/2000 | Tetzlaff et al. | |
| 6,223,100 B1 | 4/2001 | Green | |
| D449,886 S | 10/2001 | Tetzlaff et al. | |
| D457,958 S | 5/2002 | Dycus et al. | |
| D457,959 S | 5/2002 | Tetzlaff et al. | |
| 6,432,112 B2 | 8/2002 | Brock et al. | |
| 6,461,352 B2 | 10/2002 | Morgan et al. | |
| 6,626,901 B1 | 9/2003 | Treat et al. | |
| 6,689,131 B2 * | 2/2004 | McClurken | 606/48 |
| 6,743,239 B1 | 6/2004 | Kuehn et al. | |
| D493,888 S | 8/2004 | Reschke | |
| 6,775,575 B2 * | 8/2004 | Bommannan et al. | 607/101 |
| D496,997 S | 10/2004 | Dycus et al. | |
| D499,181 S | 11/2004 | Dycus et al. | |
| 6,860,880 B2 | 3/2005 | Treat et al. | |
| D509,297 S | 9/2005 | Wells | |
| D525,361 S | 7/2006 | Hushka | |
| 7,107,124 B2 | 9/2006 | Green | |
| D531,311 S | 10/2006 | Guerra et al. | |
| 7,137,980 B2 | 11/2006 | Buysse et al. | |
| D533,942 S | 12/2006 | Kerr et al. | |
| D535,027 S | 1/2007 | James et al. | |
| 7,156,842 B2 | 1/2007 | Sartor et al. | |
| 7,179,255 B2 | 2/2007 | Lettice et al. | |
| D541,418 S | 4/2007 | Schechter et al. | |
| D541,938 S | 5/2007 | Kerr et al | |
| 7,248,944 B2 | 7/2007 | Green | |
| 7,318,823 B2 | 1/2008 | Sharps et al. | |
| D564,662 S | 3/2008 | Moses et al. | |
| 7,344,268 B2 | 3/2008 | Jigamian | |
| D567,943 S | 4/2008 | Moses et al. | |
| D574,323 S | 8/2008 | Waaler | |
| D575,395 S | 8/2008 | Hushka | |
| D575,401 S | 8/2008 | Hixson et al. | |
| 7,887,536 B2 | 2/2011 | Johnson et al. | |
| 8,016,827 B2 | 9/2011 | Chojin | |
| 8,112,871 B2 | 2/2012 | Brandt et al. | |
| 8,114,122 B2 | 2/2012 | Nau, Jr. | |
| 8,133,254 B2 | 3/2012 | Dumbauld et al. | |
| 8,142,473 B2 | 3/2012 | Cunningham | |
| 8,162,965 B2 | 4/2012 | Reschke et al. | |
| 8,162,973 B2 | 4/2012 | Cunningham | |
| 8,197,479 B2 | 6/2012 | Olson et al. | |
| 8,226,650 B2 | 7/2012 | Kerr | |
| 8,251,994 B2 | 8/2012 | McKenna et al. | |
| 8,257,387 B2 | 9/2012 | Cunningham | |
| 8,266,783 B2 | 9/2012 | Brandt et al. | |
| 2003/0069571 A1 | 4/2003 | Treat et al. | |
| 2003/0216732 A1 | 11/2003 | Truckai et al. | |
| 2004/0015163 A1 * | 1/2004 | Buysse et al. | 606/34 |
| 2005/0033278 A1 | 2/2005 | McClurken et al. | |
| 2007/0016182 A1 | 1/2007 | Lipson et al. | |
| 2007/0173811 A1 * | 7/2007 | Couture et al. | 606/39 |
| 2007/0260235 A1 | 11/2007 | Podhajsky | |
| 2010/0016857 A1 | 1/2010 | McKenna et al. | |
| 2010/0023009 A1 | 1/2010 | Moses et al. | |
| 2010/0036375 A1 | 2/2010 | Regadas | |
| 2010/0042143 A1 | 2/2010 | Cunningham | |
| 2010/0049187 A1 | 2/2010 | Carlton et al. | |
| 2010/0057081 A1 | 3/2010 | Hanna | |
| 2010/0057082 A1 | 3/2010 | Hanna | |
| 2010/0057083 A1 | 3/2010 | Hanna | |
| 2010/0057084 A1 | 3/2010 | Hanna | |
| 2010/0063500 A1 | 3/2010 | Muszala | |
| 2010/0069903 A1 | 3/2010 | Allen, IV et al. | |
| 2010/0069904 A1 | 3/2010 | Cunningham | |
| 2010/0069953 A1 | 3/2010 | Cunningham | |
| 2010/0076427 A1 | 3/2010 | Heard | |
| 2010/0076430 A1 | 3/2010 | Romero | |
| 2010/0076431 A1 | 3/2010 | Allen, IV | |
| 2010/0076432 A1 | 3/2010 | Horner | |
| 2010/0087816 A1 | 4/2010 | Roy | |
| 2010/0094287 A1 | 4/2010 | Cunningham et al. | |
| 2010/0100122 A1 | 4/2010 | Hinton | |
| 2010/0179545 A1 | 7/2010 | Twomey et al. | |
| 2010/0179546 A1 | 7/2010 | Cunningham | |
| 2010/0179547 A1 | 7/2010 | Cunningham et al. | |
| 2010/0249769 A1 | 9/2010 | Nau, Jr. et al. | |
| 2010/0274244 A1 | 10/2010 | Heard | |
| 2010/0280511 A1 | 11/2010 | Rachlin et al. | |
| 2011/0015632 A1 | 1/2011 | Artale | |
| 2011/0034918 A1 | 2/2011 | Reschke | |
| 2011/0046623 A1 | 2/2011 | Reschke | |
| 2011/0054467 A1 | 3/2011 | Mueller et al. | |
| 2011/0054468 A1 | 3/2011 | Dycus | |
| 2011/0054469 A1 | 3/2011 | Kappus et al. | |
| 2011/0054471 A1 | 3/2011 | Gerhardt et al. | |
| 2011/0054472 A1 | 3/2011 | Romero | |
| 2011/0060333 A1 | 3/2011 | Mueller | |
| 2011/0060334 A1 | 3/2011 | Brandt et al. | |
| 2011/0060335 A1 | 3/2011 | Harper et al. | |
| 2011/0071523 A1 | 3/2011 | Dickhans | |
| 2011/0077648 A1 | 3/2011 | Lee et al. | |
| 2011/0077649 A1 | 3/2011 | Kingsley | |
| 2011/0082457 A1 | 4/2011 | Kerr et al. | |
| 2011/0082494 A1 | 4/2011 | Kerr et al. | |
| 2011/0087221 A1 | 4/2011 | Siebrecht et al. | |
| 2011/0098689 A1 | 4/2011 | Nau, Jr. et al. | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2602517 | 7/1976 |
| DE | 2504280 | 8/1976 |
| DE | 2514501 | 10/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3423356 | 6/1986 |
| DE | 3510586 | 10/1986 |
| DE | 3612646 | 4/1987 |
| DE | 3604823 | 8/1987 |
| DE | 8712328 | 3/1988 |
| DE | 390937 | 4/1989 |
| DE | 3904558 | 8/1990 |
| DE | 3942998 | 7/1991 |
| DE | 4206433 | 9/1993 |
| DE | 4303882 | 8/1994 |
| DE | 4339049 | 5/1995 |
| DE | 4403252 | 8/1995 |
| DE | 19515914 | 7/1996 |
| DE | 195 06 363 | 8/1996 |
| DE | 19506363 | 8/1996 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19848540 | 5/2000 |
| DE | 10045375 | 10/2002 |
| DE | 19738457 | 1/2009 |
| EP | 246350 | 11/1987 |
| EP | 267403 | 5/1988 |

(56) References Cited

FOREIGN PATENT DOCUMENTS

| | | |
|---|---|---|
| EP | 310431 | 4/1989 |
| EP | 325456 | 7/1989 |
| EP | 336742 | 10/1989 |
| EP | 390937 | 10/1990 |
| EP | 0589555 | 7/1993 |
| EP | 556705 | 8/1993 |
| EP | 0589555 | 3/1994 |
| EP | 608609 | 8/1994 |
| EP | 836868 | 4/1998 |
| EP | 882955 | 12/1998 |
| EP | 1051948 | 11/2000 |
| EP | 1159926 | 12/2001 |
| EP | 1 278 007 | 1/2003 |
| EP | 1278007 | 1/2003 |
| EP | 1 609 430 | 12/2005 |
| EP | 1609430 | 12/2005 |
| EP | 1366724 | 1/2006 |
| EP | 880220 | 6/2006 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 166452 | 1/1965 |
| SU | 401367 | 11/1974 |
| SU | 727201 | 4/1980 |
| WO | WO 92/04873 | 4/1992 |
| WO | WO92/04873 | 4/1992 |
| WO | WO99/03407 | 1/1999 |
| WO | WO 99/03407 | 1/1999 |
| WO | WO99/03408 | 1/1999 |
| WO | WO 99/03408 | 1/1999 |
| WO | WO 99/03409 | 1/1999 |
| WO | WO99/03409 | 1/1999 |
| WO | WO 00/36986 | 6/2000 |
| WO | WO 01/01847 | 1/2001 |
| WO | WO01/01847 | 1/2001 |
| WO | WO 01/54604 | 8/2001 |
| WO | WO02/11634 | 2/2002 |
| WO | WO02/45589 | 6/2002 |
| WO | WO03/090635 | 11/2003 |
| WO | WO 2005/110264 | 11/2005 |
| WO | WO2006/050888 | 5/2006 |

OTHER PUBLICATIONS

Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep., 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul., 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.

(56) References Cited

OTHER PUBLICATIONS

International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09009860 dated Dec. 8, 2009.
International Search Report EP09164754.5 dated Aug. 21, 2009.
International Search Report EP09169377.0 dated Dec. 15, 2009.
International Search Report EP09172749.5 dated Dec. 4, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
C. Gabriel, "Comments on 'Dielectric Properties of the Skin'", Phys. Med. Biol. 42 (1997), pp. 1671-1674.
Robert H. Cole; "Evaluation of Dielectric Behavior by Time Domain Spectroscopy. II. Complex Permittivity", The Journal of Physical Chemistry, vol. 79, No. 14, 1975 pp. 1469-1474.
Fujimoto et al., "Femtosecond Optical Ranging in Biological Systems", Optics Letters, vol. 11, No. 3, Mar. 1986 pp. 150-152.
Taroni et al. "In Vivo Absorption and Scattering Spectroscopy of Biological Tissues", The Royal Society of Chemistry and Owner Societies 2003; Photochem. Photobiol. Sci. 2003, 2 pp. 124-129.
Aamodt et al., "In Vivo Brain Tissue Water Measurement", 17th Southern Biomedical Engineering Conference; 1998 p. 115.
Naito et al., "In Vivo Dielectric Analysis of Free Water Content of Biomaterials by Time Domain Reflectometry", Biological Science Laboratories, Kao Corporation, 2606 Akabane, Ichikai, Haga Tochigi 321-34, Japan; Dept. of Physics, Tokai University, Hiratsuka, Kanagawa 259-12, Japan (Apr. 7, 1997) pp. 163-172.
Athey et al., "Measurement of Radio Frequency Permittivity of Biological Tissues With an Open-Ended Coaxial Line: Part 1", IEEE Transactions on Microwave Theory and Techniques, vol. MTT-30, No. 1, Jan. 1982. pp. 82-86.
Athey et al., "Measurement of Radio Frequency Permittivity of Biological Tissues With an Open-Ended Coaxial Line: Part II", IEEE Transactions on Microwave Theory and Techniques, vol. MTT-30, No. 1, Jan. 1982. pp. 87-92.
Yagihara et al., "Microwave Dielectric Study on Water Structure and Physical Properties of Aqueous Systems Using Time Domain Reflectometry With Flat-End Cells", Subsurface Sensing Technologies and Applications, vol. 2, No. 1, (2001) pp. 15-30.
C. Gabriel, "The Dielectric Properties of Biological Tissues: I. Literature Survey", Phys. Med. Biol. 41 (1996) pp. 2231-2249.
C. Gabriel, "The Dielectric Properties of Biological Tissues: II. Measurements in the Frequency Range 10 Hz to 20 GHz", Phys. Med. Biol. 41 (1996) pp. 2251-2269.
C. Gabriel, "The Dielectric Properties of Biological Tissues: III. Parametric Models for the Dielectric Spectrum of Tissues", Phys. Med. Biol. 41 (1996) pp. 2271-2293.

Feldman et al., "Time Domain Dielectric Spectroscopy Study of Biological Systems", IEEE Transactions on Dielectrics and Electrical Insulation, vol. 10, No. 5, Oct. 2003, pp. 728-753.
Miura et al., "Time Domain Reflectometry: Measurement of Free Water in Normal Lung and Pulmonary Edema", American Journal Lung Cellular Molecular Physiology 276, The American Physiological Society, Bethesda MD, (1999) pp. 207-212.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.

(56) References Cited

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Int'l Search Report dated Apr. 24, 2008 from counterpart PCT/US08/052460 filed Jan. 1, 2008.
U.S. Appl. No. 10/406,690, Apr. 3, 2003, Klicek.
U.S. Appl. No. 10/573,713, Mar. 28, 2006, Wham et al.
U.S. Appl. No. 11/242,458, Oct. 3, 2005, Becker et al.
U.S. Appl. No. 12/136,620, Jun. 10, 2008, Podhajsky et al.
U.S. Appl. No. 12/184,556, Aug. 1, 2008, Paulus.
U.S. Appl. No. 12/203,734, Sep. 3, 2008, Behnke et al.
U.S. Appl. No. 12/205,298, Sep. 5, 2008, Orszulak.
U.S. Appl. No. 12/205,525, Sep. 5, 2008, Orszulak.
U.S. Appl. No. 12/241,861, Sep. 30, 2008, Haley et al.
U.S. Appl. No. 12/241,905, Sep. 30, 2008, Brannan et al.
U.S. Appl. No. 12/241,942, Sep. 30, 2008, Brannan et al.

(56) References Cited

OTHER PUBLICATIONS

U.S. Appl. No. 12/241,983, Sep. 30, 2008, Brannan et al.
U.S. Appl. No. 12/242,026, Sep. 30, 2008, Brannan et al.
U.S. Appl. No. 12/242,061, Sep. 30, 2008, Brannan et al.
U.S. Appl. No. 12/242,102, Sep. 30, 2008, Brannan et al.
U.S. Appl. No. 12/249,218, Oct. 10, 2008, Kerr.
U.S. Appl. No. 12/249,263, Oct. 10, 2008, Ward et al.
U.S. Appl. No. 12/351,935, Jan. 12, 2009, Podhajsky et al.
U.S. Appl. No. 12/351,947, Jan. 12, 2009, Podhajsky.
U.S. Appl. No. 12/351,960, Jan. 12, 2009, Podhajsky et al.
U.S. Appl. No. 12/351,970, Jan. 12, 2009, Podhajsky et al.
U.S. Appl. No. 12/351,980, Jan. 12, 2009, Podhajsky et al.
U.S. Appl. No. 12/353,002, Jan. 13, 2009, Joseph et al.
U.S. Appl. No. 12/353,012, Jan. 13, 2009, Joseph et al.
U.S. Appl. No. 12/407,896, Mar. 20, 2009, Craig.
U.S. Appl. No. 12/477,245, Jun. 3, 2009, Podhajsky.
U.S. Appl. No. 12/481,087, Jun. 9, 2009, Odom.
U.S. Appl. No. 12/534,308, Aug. 3, 2009, Gilbert.
U.S. Appl. No. 12/540,190, Aug. 12, 2009, Gilbert.
U.S. Appl. No. 12/549,563, Aug. 28, 2009, Gilbert.
U.S. Appl. No. 12/556,770, Sep. 10, 2009, Gilbert et al.
U.S. Appl. No. 12/566,173, Sep. 24, 2009, Gilbert.
U.S. Appl. No. 12/566,233, Sep. 24, 2009, Gregg.
U.S. Appl. No. 12/567,966, Sep. 28, 2009, Keller.
U.S. Appl. No. 12/613,876, Nov. 6, 2009, Keller.

\* cited by examiner

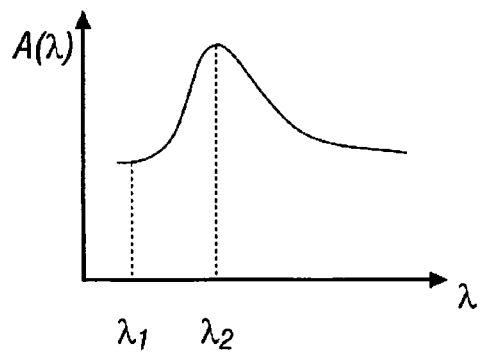 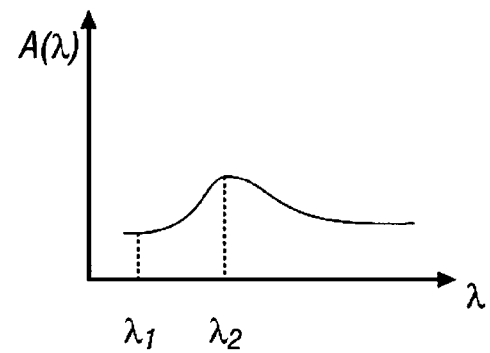
*FIG. 4A*          *FIG. 4B*
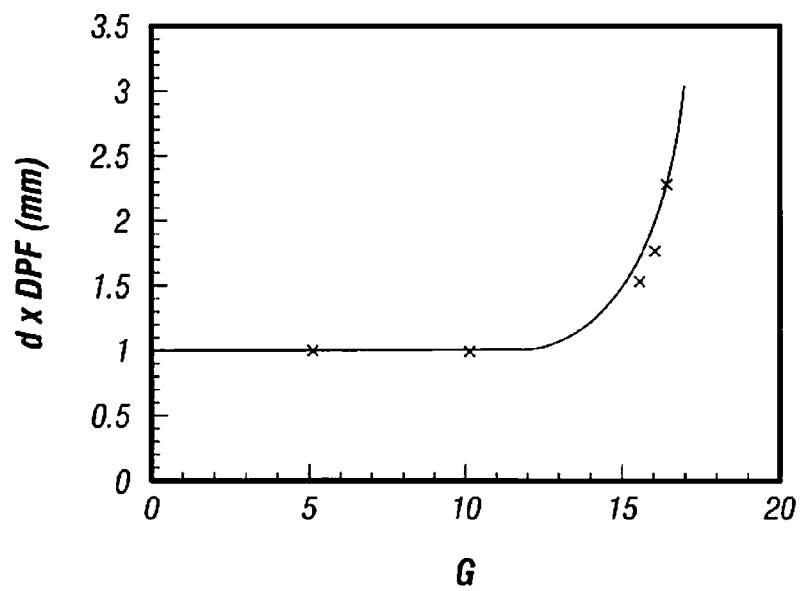
*FIG. 5*

METHOD AND SYSTEM FOR MONITORING TISSUE DURING AN ELECTROSURGICAL PROCEDURE

CROSS-REFERENCE TO RELATED APPLICATIONS

This application claims the benefit of priority to U.S. Provisional Patent Application Ser. No. 60/937,707 filed on Jun. 29, 2007 by Syms et al, entitled "METHOD AND SYSTEM FOR MONITORING TISSUE DURING AN ELECTROSURGICAL PROCEDURE", which is incorporated by reference herein.

BACKGROUND

1. Technical Field

The following disclosure relates to a system and method for monitoring macroscopic tissue modifications during an electrosurgical procedure, and more particularly to a system and method that quantifies the progress of tissue thermal damage and dehydration using optical monitoring.

2. Description of Related Art

Electrosurgical forceps use a combination of mechanical pressure and electrical energy to effect hemostasis, by heating tissue and blood vessels to coagulate, cauterize and/or seal tissue. By controlling the power, frequency and duration of the electrical energy delivered to the tissue, a surgeon can cauterise, coagulate, desiccate and/or slow bleeding. However, the delivered energy must be controlled in real-time as a function of the tissue state so that a reliable and reproducible surgical effect is generated.

To resolve the issues above and other issues relevant to coagulation and other tissue treatments, Valleylab Inc. (a division of Tyco Healthcare LP) has developed a technology called vessel or tissue sealing. Electrosurgical vessel sealing is fundamentally different from the process of coagulating vessels. For the purposes herein, "coagulation" is defined as a process of desiccating tissue wherein the tissue cells are ruptured and dried. Vessel sealing is defined as a process of liquefying collagen in tissue, so that it forms a fused mass with limited demarcation and capable of joining opposing tissue structures to seal a large vessel.

It is known in the art that the radio frequency (RF) energy delivery, the distance between jaw members in the sealing device and the pressure exerted by the jaw members must be controlled. In this way, the optimum tissue transformations leading to a seal can be generated, and hence a reproducible reliable seal can be achieved.

Two macroscopic effects that are induced in tissue during the RF tissue fusion process are thermal damage and dehydration. For the purposes herein, the term "thermal damage" is used to describe any bio-structural alteration of the tissue induced by heat. Thermal damage generally includes several biophysical modifications of the tissue that can ultimately lead to tissue death or denaturation—the loss of tridimensional protein structure.

The energy delivered to the tissue during an electrosurgical procedure and the consequent tissue transformations must be controlled and terminated so that a reliable seal is achieved. Historically, it was the responsibility of the surgeon to control and terminate the delivery of energy when the desired effect was produced. The experience of the surgeon was therefore of paramount importance. In the late 1980s, feedback controlled energy sources were introduced, in an effort to eliminate the need for empirical operation. For example, modifications to the tissue electrical impedance have been used as a feedback parameter in RF tissue fusion. Similarly, modifications to the optical properties of the tissue have been suggested to measure transformations induced by laser processing. Each of these methods has some drawbacks.

For example, impedance is often used to control the delivery of RF energy during tissue fusion, because it is relatively easy to measure and because dehydration is believed to reduce conductivity and, hence, increase impedance during the final stage of the fusion process. However, hydration does not completely correlate to impedance. As a result, impedance tends to be a less useful control parameter for the overall tissue sealing process.

Optical spectroscopy has the potential to provide more detailed information on the overall state of the tissue, since it allows information to be gathered on both the tissue structure and the tissue's biochemical makeup. In this case, there are much more significant meteorological challenges, since the detectable signals are generally very weak. Further, algorithms are typically required to extract directly relevant information about the tissue-state from the raw optical signals.

Various prior art patents have proposed the use of optical measurements to control the delivery of energy during an electrosurgical procedure, e.g., U.S. Pat. Nos. 5,762,609; 5,769,791; 5,772,597; and 5,785,658 to Benaron. These references disclose that signals can be measured either at or inside the surface of the tissue and that spectroscopy may be utilized in transmission or in reflection to monitor the signal. However, experiments show that the very large changes in scattering that occur in tissue can cause the signal detected by either method to be effectively extinguished during different stages of a thermal process, so that neither method on its own can provide continuous feedback. The systems proposed by Benaron also use raw optical parameters to control the electrosurgical generator, rather than extracted parameters such as thermal damage and tissue hydration.

SUMMARY OF THE INVENTION

The object of the present invention is to provide a more accurate system and method of optically monitoring and controlling the RF tissue fusion processes. The system and method disclosed herein is based on a system that combines transmission and reflection spectroscopy to provide continuous data with an algorithm for accurate quantification of components such as water even in tissue with strongly varying scattering properties.

A system for monitoring tissue modifications during an electrosurgical procedure is disclosed. The system includes an electrical generator for generating RF energy and an electrosurgical apparatus including a pair of jaw members configured to grasp tissue therebetween, deliver RF energy to the tissue, and allow optical measurement of the tissue state by transmission and reflection spectroscopy.

The present disclosure relates to a system for monitoring and controlling tissue modification during an electrosurgical procedure and includes an electrosurgical apparatus that couples to an electrosurgical generator for generating electrical energy. The electrosurgical apparatus, e.g., a forceps, includes a pair of jaw members configured to grasp tissue therebetween and allow light transmission therethrough. The jaw members (or a portion thereof) may be transparent or translucent to accomplish this purpose. The system also includes an optical system having one or more optical sources which generate light (e.g., an optical transmission signal) of one or more wavelengths. At least a portion of the light is transmitted through tissue and at least a portion of the light is reflected from the tissue.

One or more optical detectors are included and are configured to analyze the portion of the light of being transmitted through tissue. The same or a different optical detector is configured to analyze the portion of the light being reflected from the tissue. A processor is operatively coupled to the optical system and to the electrosurgical generator and is configured to control the delivery of electrical energy from the electrosurgical generator to tissue based on information provided by the optical system by the detector(s).

In one embodiment, the optical system controls the electrosurgical generator in real time during the electrosurgical procedure. In another embodiment, the optical system detects thermal damage of tissue and/or hydration of tissue and cooperates with the electrosurgical generator via the processor to control the delivery of electrical energy to the tissue. The optical system may include a continuous wave device, a superluminescent light-emitting diode array and/or an incandescent lamp.

In still another embodiment, the optical system operatively connects to one or more optical fibres disposed through the electrosurgical apparatus. In yet another embodiment, the optical system includes one or more lenses for transmitting light therethrough. The optical system may also include a light delivery system and a light collection system, one or both of which being disposed fully or partially within the electrosurgical apparatus.

In embodiments, two different optical detectors may be utilized with the processor to analyze the signals—one to analyze transmitted signals and one to analyze reflected signals. For example, a Fabry-Perot interferometer or a dispersive spectrometer may be utilized as an optical detector.

The present disclosure also relates to a method for monitoring and controlling the delivery of electrosurgical energy to tissue during an electrosurgical procedure and includes the steps of: providing an electrosurgical apparatus including a pair of jaw members configured to grasp tissue therebetween and allow light transmission therethrough; generating electrical energy through tissue held between jaw members; generating light of one or more wavelengths at tissue; analyzing a spectral content of the light being transmitted through tissue and providing information relating thereto back to a processor; analyzing a spectral content of the light being reflected from the tissue and providing information relating thereto back to the processor; and controlling the delivery of electrical energy from the electrosurgical generator to tissue based information provided to the processor.

The present disclosure also relates to a method for monitoring and/or controlling the delivery of electrosurgical energy to tissue during an electrosurgical procedure, the method includes the steps of: directing electrosurgical energy from an electrosurgical generator through tissue; directing an optical transmission signal of at least one wavelength into tissue; analyzing the strength of the optical transmission signal and determining if the optical transmission signal is below a predetermined detection limit; analyzing a spectral content of the optical transmission signal transmitted through tissue and providing information relating thereto back to a processor to control the delivery of electrosurgical energy to tissue based on the information provided to the processor until the strength of the optical transmission signal falls below the predetermined detection limit; and analyzing the spectral content of the optical transmission signal reflected from the tissue and providing information relating thereto back to the processor to control the delivery of electrosurgical energy to tissue based on the information provided to the processor.

In one embodiment, once the strength of the optical transmission signal rises above the predetermined detection limit, the processor resumes controlling the delivery of electrosurgical energy based on the optical transmission signal being transmitted through tissue until the electrosurgical procedure is completed.

BRIEF DESCRIPTION OF THE DRAWINGS

The objects and features of the present disclosure are set forth with particularity in the appended claims. The present disclosure, both as to its organization and manner of operation, together with further objectives and advantages, may be best understood by reference to the following description, taken in connection with the accompanying drawings, as set forth below, wherein:

FIG. 4A is a graph showing the measurement of attenuation taken at $\lambda_1$ and $\lambda_2$ when reflection spectroscopy is within the detection limit and transmission spectroscopy is outside the detection limit according to an embodiment of the present disclosure;

FIG. 4B is graph showing the measurement of attenuation taken at $\lambda_1$ and $\lambda_2$ when transmission spectroscopy is within the detection limit and reflection spectroscopy is outside the detection limit according to an embodiment of the present disclosure;

FIG. 5 is a graph showing a theoretical representation of the product "d×DPF" with scattering loss "G" as obtained by a Monte Carlo Simulation according to an embodiment of the present disclosure;

DETAILED DESCRIPTION

The drawings will be better understood with reference to the following description. However, the disclosed embodiments are merely exemplary. The specific details disclosed should not be interpreted as limiting, but merely provide a basis for the claims and for teaching one skilled in the art to variously employ the invention.

Generally, the present invention provides a system and method for optical monitoring of tissue during a RF tissue procedure, by using continuous-wave transmission and reflection spectroscopy at different times to detect changes in scattering and in the absorption band associated with the vibration of water molecules near 1.45 µm wavelength. Processing of the transmission spectroscopy data allows the progress of both thermal damage and dehydration to be evaluated, thus providing a more accurate analysis of how the tissue is transformed during the fusion process. Such an analysis may allow improved understanding of the tissue modifications that lead to the high fusion quality. Processing of the reflection spectroscopy data allows control to be maintained, after it has been effectively extinguished due to increased scattering. The processed data obtained during the fusion process may be incorporated into a suitable feedback loop to control delivery of RF energy so that the optimum tissue transformations are obtained.

Figure 1:
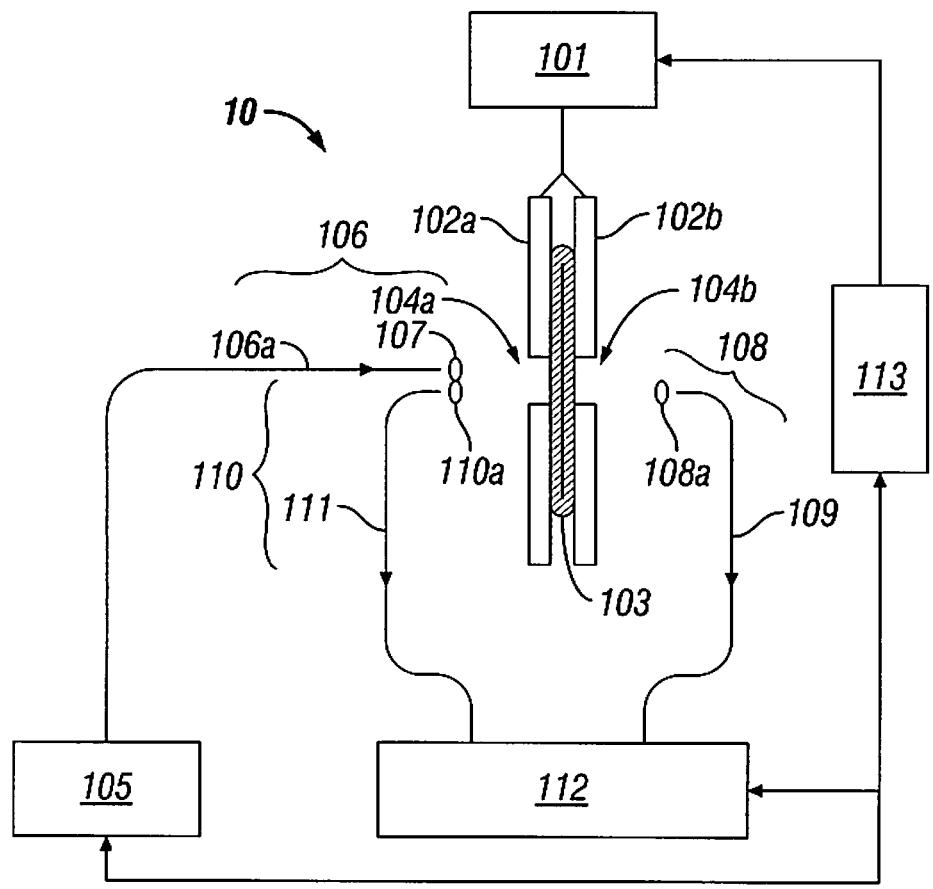
FIG. 1 is a block diagram illustrating the components of a system for monitoring and controlling tissue during an electrosurgical procedure in accordance with an embodiment of the present disclosure.

FIG. 1 shows the overall system 10, which includes an electrosurgical generator 101 operatively coupled to an electrosurgical instrument 200, represented here by a pair of jaws 102a, 102b. The electrosurgical instrument 200 is used to grasp a portion of tissue 103 and carry out an electrosurgical procedure thereon. The jaws 102a, 102b define openings 104a, 104b therein that are configured to allow the transmission of light therethrough, so that optical measurements may be performed on the grasped tissue 103 during the electrosurgical procedure.

The system 10 also includes an optical source 105 that is configured to generate broadband light and a beam delivery system 106, which in the embodiment shown includes of an optical fibre 106a and a collimating lens 107. A first portion of the light is transmitted through the tissue 103 via the openings 104a, 104b, where the light enters a first light collection system 108, which in the embodiment shown includes lens 108a and an optical fibre 109. A second portion of the light is reflected or back-scattered from the tissue 103, where it enters a second light collection system 110, which in the embodiment shown again consists of a lens 110a and an optical fibre 111. The fibres 109 and 111 are connected to an optical detection device 112, which is arranged to analyze separately the spectral content of the light transmitted and reflected from the tissue 103.

Other alternative optical arrangements are contemplated by the present disclosure that have the same or similar function. For example, the reflected or back-scattered light may be collected by the illumination lens 107 and illumination fibre 106 in a confocal arrangement, eliminating the need for the lens 110 and fibre 111. The reflected or back-scattered light may then be separated and passed to the detector 112 using a beam-splitting device. Such methods may be used without significant changes to the optical measurement scheme or to the subsequent data processing.

The system 10 also includes a processor 113 that is operatively coupled to the optical source 105 and the optical detection device 112 for transmitting instructions and data therebetween. The processor 113 is also coupled to the electrosurgical generator 101 and power output may be adjusted based on information derived from the data received from the optical detection device 112.

The electrosurgical generator 101 is operatively coupled to the electrosurgical apparatus for the purpose of performing an electrosurgical procedure such as sealing, cutting, coagulating, desiccating and fulgurating tissue using RF energy. The electrosurgical apparatus can be any suitable type of electrosurgical apparatus, including but not limited to, apparatuses that can grasp tissue and/or perform any of the above mentioned procedures. One suitable type of apparatus may include bipolar forceps, for example as disclosed in U.S. Patent Application Publication No. 2007/0173814 A1. A brief discussion of bipolar forceps 200 is included herein to aid in understanding of the present disclosure.

Figure 2:
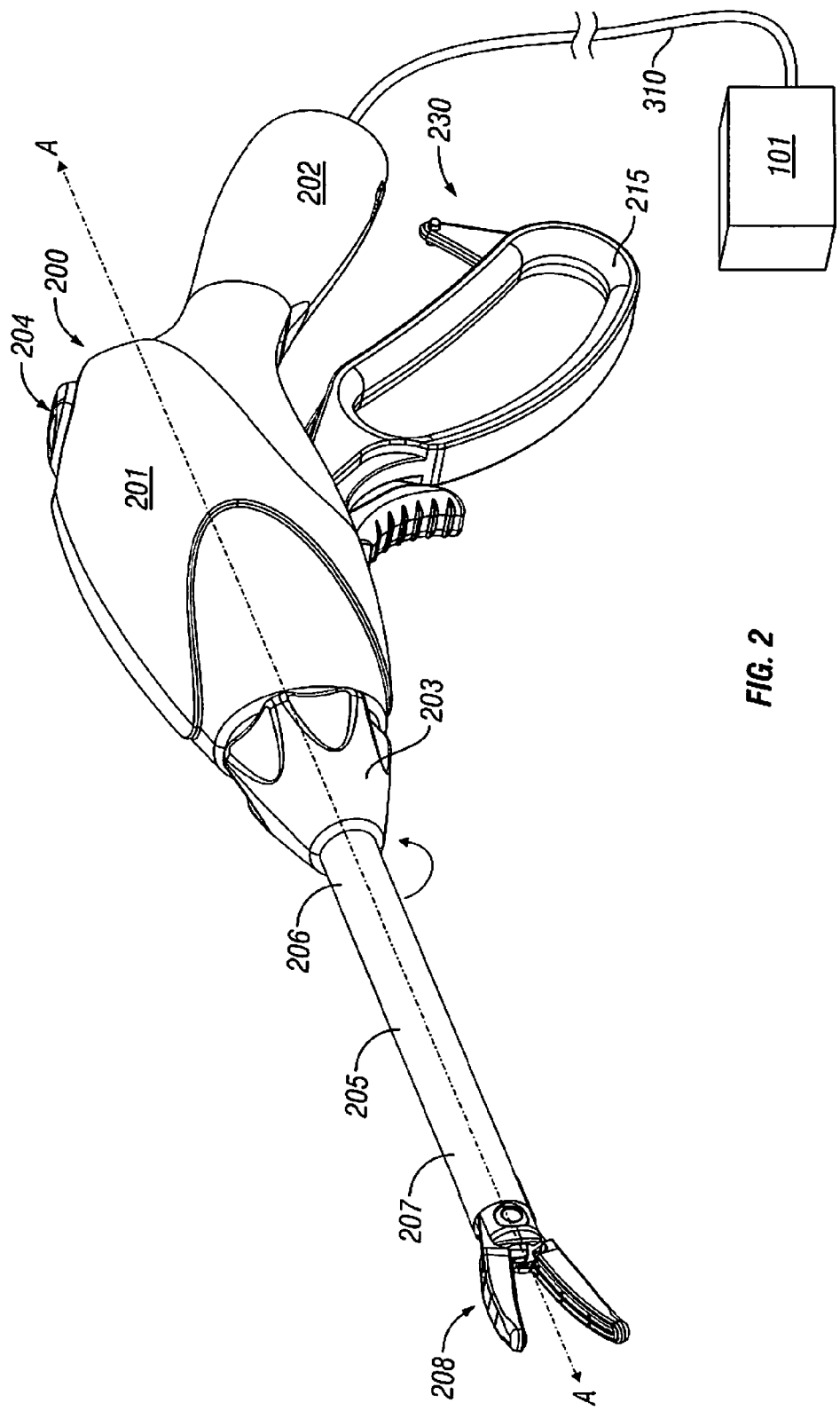
FIG. 2 is a perspective view of an endoscopic bipolar forceps shown in an open configuration according to an embodiment of the present disclosure.
Figure 3:
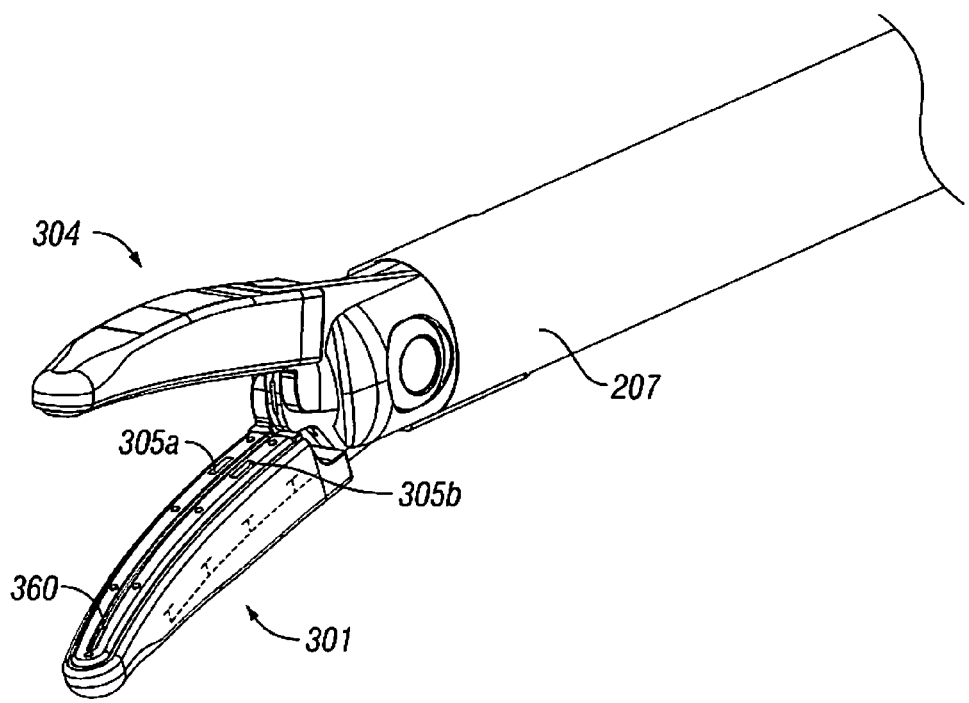
FIG. 3 is an enlarged, front perspective view of the end effector assembly of FIG. 2.

FIGS. 2 and 3 show one embodiment of a bipolar electrosurgical forceps 200 which includes a housing 201, a handle assembly 230, a rotating assembly 203, a trigger assembly 204 and a shaft 205. The shaft has a proximal end 206 that mechanically engages the rotating assembly 203, and a distal end 207 that engages an end effector assembly 208. Here, the term "proximal" refers to a component closest to the user, while the term "distal" refers to a component furthest from the user.

Forceps 200 also includes an electrosurgical cable 310 which connects the forceps 200 to a source of electrosurgical energy, e.g., a generator 101 (shown schematically). It is contemplated that generators such as those sold by Valleylab—a division of Tyco Healthcare LP, located in Boulder Colo. may be used as a source of electrosurgical energy, e.g., LigaSure™ Generator, FORCE EZ™ Electrosurgical Generator, FORCE FX™ Electrosurgical Generator, FORCE 1C™, FORCE 2™ Generator, SurgiStat™ II or other envisioned generators which may perform different or enhanced functions. One such system is described in commonly-owned U.S. Pat. No. 6,033,399 entitled "ELECTROSURGICAL GENERATOR WITH ADAPTIVE POWER CONTROL". Other systems have been described in commonly-owned U.S. Pat. No. 6,187,003 entitled "BIPOLAR ELECTROSURGICAL INSTRUMENT FOR SEALING VESSELS". As discussed in more detail below, generator 101 may include all components and parts as needed for system 10 to function and operate as intended.

Cable 310 may be internally divided into one or more cable leads (not shown) that are designed to transmit electrical potentials through their respective feed paths through the forceps 200 to the end effector assembly 208 such that upon activation of a switch 204 (See FIG. 2), energy is transmitted from the various cable leads to the respective feed paths and energy is transmitted through the tissue.

Handle assembly 230 includes a fixed handle 202 and a movable handle 215. Fixed handle 202 is integrally associated with housing 201 and handle 215 is movable relative to fixed handle 202. Rotating assembly 203 is operatively associated with the housing 201 and is rotatable approximately about a longitudinal axis "A-A" defined through the shaft 205.

As mentioned above, end effector assembly 208 is attached at the distal end 207 of shaft 205 and includes a pair of opposing jaw members 301 and 304. Movable handle 215 of handle assembly 230 is ultimately connected to a drive assembly (not shown) which, together, mechanically cooperate to impart movement of the jaw members 301 and 304 from an open position wherein the jaw members 301 and 304 are disposed in spaced relation relative to one another, to a clamping or closed position wherein the jaw members 301 and 304 cooperate to grasp tissue therebetween.

As shown in FIG. 3, an optical transmission port 305a for the delivery of light and an optical collection port 305b for reception of reflected light 305b are defined on the first jaw member 301. Variously typed, sized and placed translucent elements may be used for this purpose and any number of ports 305a and 305b may be arranged along the jaw member 310 in a variety of different configurations depending upon a particular purpose or to achieve a particular result. In the particular arrangement shown in FIG. 3, the two ports 305a and 305b correspond to or can be synonymously associated with the single opening 104a in FIG. 1. In a similar manner, one or more collection ports (not shown) for the transmission or reception of light may be defined in the second jaw member 304 and, likewise, be correspondingly associated with single opening 104b in FIG. 1. Thus, the jaw members 301 and 304 of an electrosurgical forceps 200 may readily be adapted to provide suitably transparent light paths.

Returning to the overall system 10 in FIG. 1, the optical source 105 can be any suitable source that can produce or emit light in the wavelength range of about 1.2 µm to about 1.6 µm that straddles and includes the important water absorption band near 1.45 µm. Such sources may emit continuously over a broad spectral range. One example of a suitable compact, high-power continuous broadband source is a superluminescent diode array. However, other suitable forms of broadband source, such as incandescent lamps, may be utilized.

The continuous broadband source may also be replaced by a narrowband tuneable source, such as a tuneable laser. The use of such a source requires alteration to the detection scheme described below, but does not alter the essential nature of the measurement process and the data processing carried out thereafter.

Light from the optical source 105 can be delivered via an optical fibre 106a running through the shaft 205 to one or both jaw members 301 and 304 depending upon the particular configuration of the forceps 200. Suitable optical fibres include single- or multi-mode fibres, formed from glass or plastic. In one embodiment, the light path may be turned through approximately 90 degrees on exit from the fibre 106a and collimated by lens 107 to pass through the first translucent port 305a of the jaw member 301. Suitable components to achieve a change in direction of the optical path may include prisms, small mirrors and moulded plastic light pipes. Suitable elements to achieve collimation may include conventional lenses, ball lenses and graded index rod lenses. The lens 110a, fibre 111 and folded light path needed to collect reflected light from the second translucent port 305b may also be provided in the jaw member 301 in a similar way and using similar components. Alternatively, the translucent port 305b, lens 108a, fibre 109 and folded light path needed to collect transmitted light may also be provided in the second jaw 304 in a similar way.

Light may be delivered to and collected from the end effector assembly 208 of the forceps 200 via three optical fibres 106a, 111 and 109 conveniently arranged as a single with electrical interconnects that carry power to the RF electrodes in the jaw members 310 and 304. At a suitable distance from the forceps 200, the individual optical fibres 106a, 111 and 109 may be separated and attached to optical fibre connectors (not shown) to allow removable or selectively detachable connection to the optical source 105 and optical detection system 112.

Additional fibres (not shown) carrying additional illumination light and collecting additional transmitted and/or reflected light and data from the tissue may also be provided. These additional fibres may be used for monitoring a variety of different tissue properties at different points along one or both jaw members 301 and 304, or, alternatively, may be configured for bidirectional monitoring of the tissue.

In the embodiment shown in FIG. 1, the optical detection device 112 includes two equivalent systems for separately analysing the spectral content of the transmitted and reflected light. The nature of the detection systems depends on the type of optical source utilized. For example, for a continuous broadband source such as a superluminescent diode array, scanning or staring filters such as Fabry-Perot interferometers or dispersive spectrometers are suitable. For a tuneable narrowband source, fixed detectors are suitable.

The processor 113 may be a microprocessor, laptop or personal computer connected to the light source 105, the detection system 112 and the electrosurgical generator 101 via suitable interface buses that allow transfer of command instructions and data. The processor may be configured to execute a control algorithm to start, control and stop delivery of electrical power to the electrosurgical device, e.g., forceps 200, during a RF tissue fusion operation, based on feedback parameters obtained by processing data acquired in real-time from the optical detection device 112.

The electrosurgical generator 101 may be a remotely controllable source of RF energy as used in electrosurgical procedures, for example as described in U.S. Pat. Nos. 6,033,399 and 6,187,003. However, it will be apparent to those skilled in the art that other generators that perform similar or enhanced functions would also be suitable.

As previously described, the system 10 is configured to monitor the state of the tissue by evaluating the progress of both thermal damage and dehydration during an RF tissue fusion operation, by quantifying changes in optical scattering and water concentration. One contemplated control algorithm and associated mathematical equation is described below; however, a plurality of other algorithms, equations and derivations exist that achieve a similar objective, and therefore the embodiment presented should be considered illustrative rather than exclusive.

In operation, opposing jaw members 301 and 304 of the forceps 200 are used to grasp an area of tissue therebetween. Before RF energy is applied, transmission spectroscopy and/or reflection spectroscopy is performed to provide initial spectral analysis and information about the grasped tissue. The raw data obtained from this initial sampling may be used to derive an initial tissue scattering loss and tissue water concentration using a modified Beer-Lambert law model and derivations therefrom (see description below). Based on this data, an initial RF delivery strategy can be predicted, and this strategy may be extended and modified to the completion of the RF tissue fusion process based on subsequent similar measurements and processing.

The Beer-Lambert law is a mathematical relation that accounts for the concentration of absorbers in a non-scattering absorbing medium to be quantified. The intensity "I" of a light beam having an initial intensity "$I_0$" transmitted through a thickness "d" of such a medium is expressed by the equation:

$$I = I_o e^{-u_a(\lambda) \cdot d} \tag{1}$$

Here "$\lambda$" is the wavelength and "$u_a(\lambda)$" is the wavelength dependent absorption coefficient of the medium. For example, in tissue, the principal contributor to absorption near 1.45 μm wavelength is water. In this range the absorption coefficient is given by:

$$u_a(\lambda) = C_w \cdot a_w(\lambda) \tag{2}$$

Here "$C_w$" is the concentration of water in the tissue and "$a_w(\lambda)$" is the specific absorption coefficient of water. For any suitable wavelength, the attenuation "$A(\lambda)$" of the transmitted light can be defined as the logarithm of the ratio of the incident intensity to the transmitted intensity, given by:

$$A(\lambda) = -\log\left(\frac{I_o}{I}\right) = C_w \cdot \alpha_w(\lambda) \cdot d \tag{3}$$

Equation 3 in principle allows the concentration of water to be quantified from measurements of the transmission. However, when the medium is scattering—as is the case with tissue—Equation 3 may no longer be valid, because any estimate of the attenuation must take into account the modifications of path length as photons are scattered, and scattered light that is no longer detected. The attenuation may then be described using the modified Beer-Lambert law expressed as:

$$A(\lambda) = -\log\left(\frac{I_o}{I}\right) = C_w \cdot \alpha_w(\lambda) \cdot d \cdot DPF + G \tag{4}$$

Here the term "DPF" is the differential path factor, which accounts for the increase of the path length of the photons in a scattering medium, and the term "G" is the scattering loss and accounts for the loss of signal due to unabsorbed scattered light that is not detected. "G" is a strong function of the geometry of the optical system. Both the "DPF" and "G" are slowly varying functions of wavelength, but may be considered to be approximately constant over the small spectral range of interest here.

FIGS. 4A and 4B show the effect of scattering on the attenuation spectrum of a medium near an absorption band. The spectrum of FIG. 4A corresponds to a medium with relatively high scattering. Here the attenuation is composed of a baseline due to scattering loss (e.g., the point labelled "$\lambda_1$"), over which an absorption band is superimposed (e.g., the point labelled "$\lambda_2$"). The spectrum of FIG. 4B corresponds to a medium with lower scattering. Here both the baseline and the height of the absorption band are reduced. The reduction in baseline follows from the reduction in scattering loss. The reduction in absorption follows from the shorter paths traveled by photons in the absorbing medium as the scattering is reduced.

Using similar data, attenuation measurements "$A(\lambda_1)$" and "$A(\lambda_2)$" can be obtained at wavelengths "$\lambda_1$" and "$\lambda_2$", At "$\lambda_1$", far away from the absorption band, Equation 4 gives:

$$A(\lambda_1) \approx G \quad (5)$$

Hence, the value of G may be estimated from the measurement "$A(\lambda_1)$".

At "$\lambda_2$", at the peak of the absorption band, re-arrangement of equation 4 gives $$C_w = \{A(\lambda_2) - G\} / \{a_w(\lambda_2) d \times DPF\} \quad (6)$$

Equation 6 allows the water concentration to be found from measurements "$A(\lambda_2)$", the calculated value of G, and the specific absorption coefficient of water "$\alpha_w$" at the wavelength "$\lambda_2$", provided the product "d×DPF" is also known.

The value of the product "d×DPF" cannot be easily measured in a direct manner. However, it can be found by numerically modelling the propagation of light in a scattering slab and subsequent coupling the scattered light into a given optical system corresponding to the equipment used. Such a simulation may be carried out using either diffusion theory or a so-called "Monte Carlo simulation".

To a reasonable approximation, what is found is that the product "d×DPF" is mainly a function of "G", independent of any absorption in the slab. FIG. 5 shows the calculated variation of "d×DPF" as a function of "G" as it relates to an optical system. For low scattering (small "G"), the product "d×DPF" is approximately constant, suggesting that the "DPF" is also constant. For higher scattering (larger G), the product "d×DPF" rises rapidly which may be built into a simple functional model. For example, in the system disclosed herein, a reasonable approximation of the variation is given by the function:

$$d \times DPF(mm) = 1 + (G/k)^n \quad (7)$$

Here k=16 and n=12.

Knowing "d×DPF", "G" and the measurement "$A(\lambda_2)$", the water concentration "$C_w$" may then be found using Equation 6. Repetitive measurement of spectral data, at least the two wavelengths "$\lambda_1$" and "$\lambda_2$", and repetitive use of Equations 5, 6 and 7 then allows both the scattering loss term "G" and the water concentration "$C_w$" to be found as a function of time through a RF tissue fusion process.

An algorithm may then be constructed to control the RF power applied to the tissue by the electrosurgical generator 101 and the electrosurgical instrument, e.g., forceps 200, so that the concentration of water in tissue is reduced at a controlled rate to a controlled final level corresponding to a controlled final hydration state.

Figure 6A:
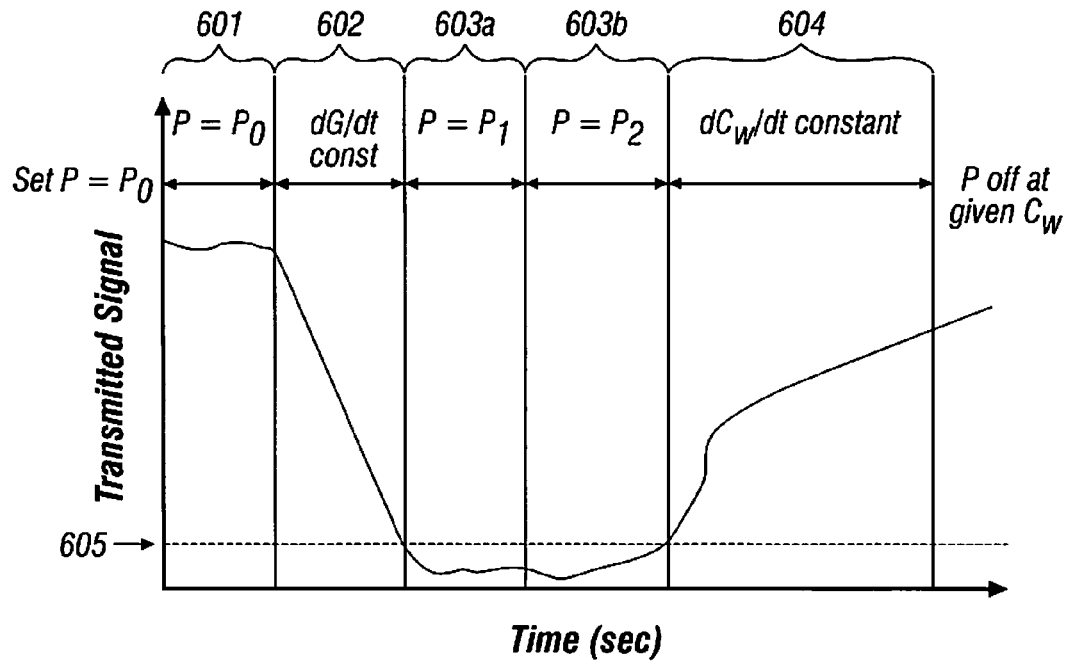
FIG. 6A is a graph showing the transmitted light signal over time during a tissue fusion process according to an embodiment of the present disclosure.

In practice, use of the algorithm may be complicated by the finite sensitivity of the measurement apparatus. For example, FIG. 6A shows a representative time variation of the transmitted signal, measured at the peak of the water absorption band, in one embodiment of a RF fusion experiment involving small bowel tissue. In the early time interval 601, the transmission is relatively high, and a usable signal is obtained. In this stage, the tissue is simply heated so that its temperature rises. However, in the time interval 602 the transmission signal falls rapidly as scattering increases due to thermal damage. In the time intervals 603a and 603b, the transmission signal is so low that it has fallen to or below the detection limit 605 of the combined optical system. In the final interval 604, when scattering typically falls due to the elimination of tissue water, the transmission rises again to a measurable level. The decrease in scattering with dehydration is explained by an increase in refractive index matching between scattering centre and ground substrate. The presence of a 'dead-band' or low detection state in which the transmitted signal is so low that the integrity of any information derived from the signal is questionable makes it difficult to formulate a reliable control algorithm for the electrosurgical generator during this time interval between 603a and 603b.

Figure 6B:
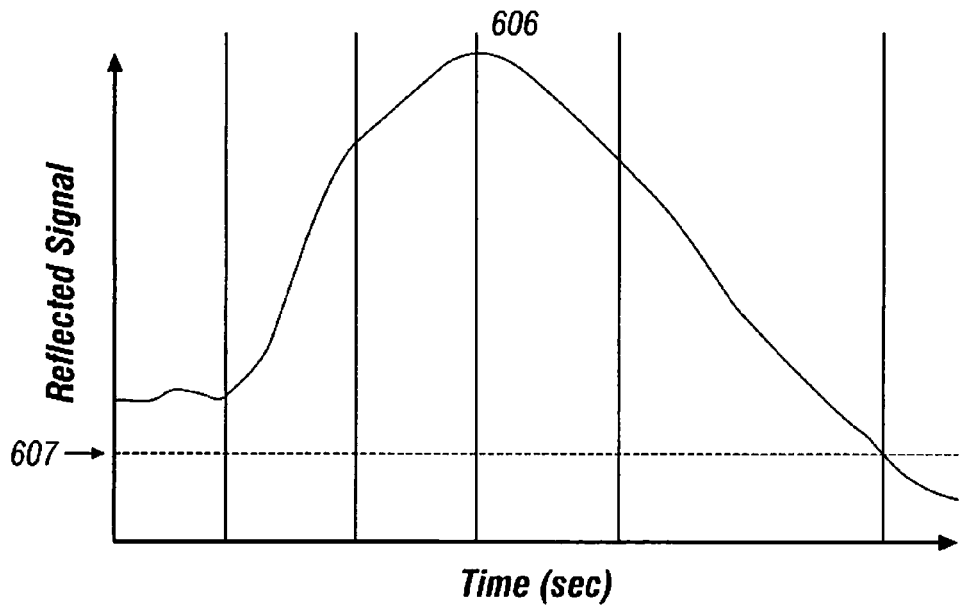
FIG. 6B is a graph showing the reflected light signal over time during a tissue fusion process according to an embodiment of the present disclosure.

A solution as presented herein is provided by utilizing the availability of the corresponding reflected signal, shown in FIG. 6B. Here the reflected signal has a low initial value in the time initial interval 601, a sharply rising value in the time interval 602 as thermal damage begins, and reaches a maximum at the time 606, when the boiling point of the water in tissue is reached. The time 606 generally approximates the midpoint of the dead-band interval between 603a and 603b. At the end of this interval, the reflected signal starts to fall as the water in tissue is boiled off, usually falling to a lower value at the end of the final interval 604 (typically below a further detection limit 607).

The availability of one or other of the transmitted and reflected signals throughout the fusion process allows a reliable control algorithm to be constructed for the electrosurgical generator. Because the two signals contain information mainly about different aspects of the tissue-state, the algorithm used to control the electrosurgical generator may be configured to optimise these different aspects separately using the two signals.

Many different possible control algorithms may exist, and therefore the example described below is intended to be illustrative rather than exclusive. For example, at the start of a tissue fusion process, and after measuring initial optical data, it may be desirable to set the average power "P" delivered by the electrosurgical generator to a maximum value "$P_0$", so that the tissue is heated rapidly to the point where tissue transformations begin. The average power "P" may be held constant at "$P_0$" throughout the time interval 601, until the transmission starts to fall. This point may be detected from the time variation of the transmitted signal.

During the time interval 602, when thermal damage is occurring, it may be desirable to reduce or control the average power "P" delivered by the electrosurgical generator so that the rate of change "dG/dt" of the extracted scattering loss parameter "G" is held at a constant value. This value may also be determined empirically. Because "G" is affected by thermal damage only, the rate of thermal damage may thereby be effectively controlled.

The algorithm used to extract the parameter "G" (See Equations 5-7) becomes unreliable when the transmitted signal reaches the detection limit 605. During the first part of the dead-band time interval 603a, before the point of maximum reflectance 606, the average power "P" delivered by the electrosurgical generator may therefore simply be held constant at "$P_1$", the power level reached at the end of the time interval 602. This strategy tends to eliminate the need to extract extraneous or potentially uncertain data from the transmitted signal.

Control is then switched and becomes a variable of the reflected signal, whose maximum 606 indicates that the boiling point of tissue water has been reached. At this point, the average power "P" delivered by the electrosurgical generator may be reduced to a lower value "$P_2$", to reduce damage caused by rapid evolution of steam within the tissue, and held constant at this level through the interval 603b.

The end of the interval 603b may be detected from a rise in the transmitted signal above the detection limit 605, and control may be passed back to data extracted from the transmitted signal. During the final interval 604, when tissue water is being driven off, it may be desirable to reduce or control the average power "P" delivered by the electrosurgical generator so that the rate of change "$dC_w/dt$" of the extracted water concentration "$C_w$" is held at a constant value. This value may also be determined empirically. The average power "P" may be switched off and the RF fusion process terminated at the end of the interval 604 when a given value "$C_w$" corresponding to a given hydration state has been reached.

In this manner, it will be apparent that control of the heating of the tissue is not only continuous, but adapted to ensure that rate of change of specific physical modifications in the tissue state may be optimised. It will also be apparent that the method of control is very flexible and may be developed further according to experience.

The present disclosure also relates to a method for monitoring and controlling the delivery of electrosurgical energy to tissue during an electrosurgical procedure and includes the steps of: providing an electrosurgical apparatus, e.g., forceps 200, including a pair of jaw members 301 and 304 configured to grasp tissue therebetween and allow light transmission therethrough; directing electrical energy from an electrosurgical generator 101 through tissue held between jaw members 301 and 304; generating light (e.g., an optical transmission signal) of one or more wavelengths at tissue; analyzing a spectral content of the light being transmitted through tissue and providing information relating thereto back to a processor 113; analyzing a spectral content of the light being reflected from the tissue and providing information relating thereto back to the processor 113; and controlling the delivery of electrical energy from the electrosurgical generator 101 to tissue based information provided to the processor 113.

The present disclosure also relates to a method for monitoring and/or controlling the delivery of electrosurgical energy to tissue during an electrosurgical procedure, the method includes the steps of: directing electrosurgical energy from an electrosurgical generator 101 through tissue; directing an optical transmission signal of at least one wavelength into tissue; analyzing the strength of the optical transmission signal and determining if the optical transmission signal is below a predetermined detection limit 605; analyzing a spectral content of the optical transmission signal transmitted through tissue and providing information relating thereto back to a processor 113 to control the delivery of electrosurgical energy to tissue based on the information provided to the processor 113 until the strength of the optical transmission signal falls below the predetermined detection limit 605; and analyzing the spectral content of the optical transmission signal reflected from the tissue and providing information relating thereto back to the processor 113 to control the delivery of electrosurgical energy to tissue based on the information provided to the processor 113.

In one embodiment, once the strength of the optical transmission signal rises above the predetermined detection limit 605, the processor 113 resumes controlling the delivery of electrosurgical energy based on the optical transmission signal being transmitted through tissue until the electrosurgical procedure is completed.

From the foregoing and with reference to the various figure drawings, those skilled in the art will appreciate that certain modifications can also be made to the present disclosure without departing from the scope of the same. For example, one or both jaw members 301 or 304 may be transparent or translucent depending upon a particular purpose.

In one embodiment, the optical system (and the various above-described optical components associated therewith) may be disposed across the two jaw members 301 and 304 with corresponding optical components in vertical or non-vertical registry depending upon a particular purpose.

Optical system 10 can also be configured to detect if tissue has been effectively cut after the tissue fusion process by utilizing one or more of the optical transmission elements and detectors as described above. That is, after an RF tissue fusion procedure has been performed, system 10 can be configured to scan the tissue or lack thereof after a cut has been performed to ensure a complete and accurate cut has been achieved. The contemplated configuration of at least four optical sources and detectors (or mirrors) may be configured to detect a portion of the light laterally (or transversally) across the tissue (e.g., across either side of a knife channel 360 as shown in FIG. 3) which can be employed to detect if the tissue has been effectively cut.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for monitoring and/or controlling tissue modification during an electrosurgical procedure comprising:
   an electrosurgical apparatus adapted to connect to an electrosurgical generator, the electrosurgical apparatus including a pair of jaw members configured to grasp tissue therebetween and allow light transmission therethrough, at least one of the jaw members having an optical transmission port and an optical collection port disposed on a tissue contacting surface thereof;
   an optical system including:
      at least one optical source configured to generate light;
      at least one optical detector configured to analyze a first portion of the light transmitted through the tissue and configured to analyze a second portion of the light reflected from the tissue; and
   a processor operatively coupled to the optical system and to the electrosurgical generator, the processor configured to control the delivery of electrosurgical energy from the electrosurgical generator to tissue based on information provided by the optical system,
   wherein the processor is programmed to sample a spectral content of the tissue held between the jaw members to obtain optical data relating to the tissue to derive an electrosurgical energy delivery strategy and to set an initial power level intensity of electrosurgical energy based on the optical data relating to the tissue,
wherein the at least one optical source operably couples to the optical transmission port and the at least one optical detector operably couples to the optical collection port.

2. The system according to claim 1, wherein the optical system is configured to control the electrosurgical generator in real-time during the electrosurgical procedure.

3. The system according to claim 1, wherein the optical system detects at least one of thermal damage of tissue and hydration of tissue and is configured to cooperate with the electrosurgical generator via the processor to control the delivery of electrosurgical energy to the tissue.

4. The system according to claim 1, wherein the optical system includes a continuous wave device.

5. The system according to claim 1, wherein the optical system includes a superluminescent light-emitting diode array.

6. The system according to claim 1, wherein the optical system includes an incandescent lamp.

7. The system according to claim 1, wherein the optical system operatively couples to at least one optical fibre disposed through the electrosurgical apparatus.

8. The system according to claim 1, wherein the optical system includes at least one lens for transmitting light therethrough.

9. The system according to claim 1, wherein the optical system includes a light delivery system and a light collection system, at least a portion of the light delivery system and at least a portion of the light collection system disposed within the electrosurgical apparatus.

10. The system according to claim 1, wherein at least a portion of at least one of the jaw members is translucent.

11. The system according to claim 1, wherein the at least one optical detector is a Fabry-Perot interferometer.

12. The system according to claim 1, wherein the at least one optical detector is a dispersive spectrometer.

13. The system according to claim 1, wherein the optical system includes:
 a first optical detector configured to analyze the first portion of the light transmitted through tissue; and
 a second optical detector configured to analyze the second portion of the light reflected from the tissue.

14. The system according to claim 1 wherein light is generated from the optical source in a wavelength range of about 1.2 µm to about 1.6 µm.

15. The system according to claim 1 wherein light is generated from the optical source in a wavelength range of 1.45 µm.

16. A method for monitoring and/or controlling the delivery of electrosurgical energy to tissue during an electrosurgical procedure, the method comprising the steps of:
 providing an electrosurgical apparatus including a pair of jaw members configured to grasp tissue therebetween and allow light transmission therethrough, at least one of the jaw members having an optical transmission port and an optical collection port disposed on a tissue contacting surface thereof;
 sampling a spectral content of tissue held between the jaw members to obtain optical data relating to the tissue to derive an electrosurgical energy delivery strategy;
 setting an initial power level intensity of electrosurgical energy based on the optical data relating to the tissue;
 directing electrosurgical energy from an electrosurgical generator at the initial power lever intensity through tissue held between jaw members;
 directing light of at least one wavelength into tissue from the optical transmission port coupled to an optical source;
 analyzing a spectral content of a first portion of the light transmitted through tissue and providing information relating thereto back to a processor;
 analyzing a spectral content of a second portion of the light reflected from the tissue with an optical detector coupled to the optical collection port and providing information relating thereto back to the processor; and
 controlling the delivery of electrosurgical energy from the electrosurgical generator to tissue based on the information provided to the processor.

17. The method of claim 16, wherein the optical detector is used to analyze the spectral content of the first and second portions of the light.

18. The method of claim 16, wherein the step of controlling the delivery of electrical energy includes at least one of reducing, increasing and stopping RF energy delivery.

19. A method for monitoring and/or controlling the delivery of electrosurgical energy to tissue during an electrosurgical procedure, the method comprising the steps of:
 sampling a spectral content of tissue held between a pair of jaw members of an electrosurgical apparatus to obtain optical data relating to the tissue to derive an electrosurgical energy delivery strategy;
 setting an initial power level intensity of electrosurgical energy based on the optical data relating to the tissue;
 directing electrosurgical energy at the initial power level intensity from the pair of jaw members through the tissue;
 directing an optical transmission signal of at least one wavelength into the tissue from an optical transmission port on at least one of the jaw members of the electrosurgical apparatus and coupled to an optical source;
 measuring a first spectral content of the optical transmission signal transmitted through the tissue and providing information relating to the first spectral content back to a processor;
 controlling the delivery of the electrosurgical energy based on the provided information relating to the first spectral content until the strength of the optical transmission signal falls below a predetermined detection limit;
 when the strength of the optical transmission signal falls below the predetermined detection limit, measuring a second spectral content of the optical transmission signal reflected from the tissue with an optical collection port on the at least one jaw member of the electrosurgical apparatus and coupled to an optical detector, and providing information relating to the second spectral content to the processor; and
 controlling the delivery of the electrosurgical energy based on the provided information relating to the second spectral content.

20. The method of claim 19 wherein after the step of measuring the second spectral content of the optical transmission signal reflected from the tissue, when the strength of the optical transmission signal rises above the predetermined detection limit, the processor resumes controlling the delivery of electrosurgical energy based on the provided information relating to the first spectral content until electrosurgical procedure is completed.

21. The method of claim 19 wherein the predetermined detection limit of the initial measuring step is proportional to the hydration level of the tissue.

* * * * *